United States Patent
Rist et al.

(10) Patent No.: US 11,596,582 B2
(45) Date of Patent: Mar. 7, 2023

(54) PARTICLES WITH IMPROVED COLOUR SHIELDING

(71) Applicant: Ivoclar Vivadent AG, Schaan (LI)

(72) Inventors: Kai Rist, Feldkirch (AT); Annette Schmidt, Cologne (DE); Ahmad Shaaban, Cologne (DE)

(73) Assignee: Ivoclar Vivadent AG, Schaan (LI)

( * ) Notice: Subject to any disclaimer, the term of this patent is extended or adjusted under 35 U.S.C. 154(b) by 726 days.

(21) Appl. No.: 16/542,408

(22) Filed: Aug. 16, 2019

(65) Prior Publication Data

US 2020/0078271 A1 Mar. 12, 2020

(30) Foreign Application Priority Data

Sep. 10, 2018 (EP) .................................. 18193477

(51) Int. Cl.
| | | |
|---|---|---|
| *A61K 6/17* | (2020.01) | |
| *A61K 6/88* | (2020.01) | |
| *A61K 6/84* | (2020.01) | |
| *A61K 6/871* | (2020.01) | |
| *A61K 6/16* | (2020.01) | |
| *A61K 6/71* | (2020.01) | |
| *H01F 1/00* | (2006.01) | |
| *A61K 6/831* | (2020.01) | |
| *A61K 6/884* | (2020.01) | |
| *C09C 1/00* | (2006.01) | |

(52) U.S. Cl.
CPC ................. *A61K 6/17* (2020.01); *A61K 6/16* (2020.01); *A61K 6/71* (2020.01); *A61K 6/831* (2020.01); *A61K 6/84* (2020.01); *A61K 6/871* (2020.01); *A61K 6/88* (2020.01); *A61K 6/884* (2020.01); *C09C 1/0051* (2013.01); *H01F 1/0054* (2013.01); *C01P 2004/62* (2013.01); *C01P 2004/64* (2013.01); *C01P 2004/80* (2013.01); *C01P 2004/84* (2013.01); *C01P 2006/42* (2013.01); *C01P 2006/60* (2013.01); *C09C 2200/1004* (2013.01); *C09C 2200/1054* (2013.01); *C09C 2200/302* (2013.01); *C09C 2200/303* (2013.01); *C09C 2200/308* (2013.01); *C09C 2210/00* (2013.01)

(58) Field of Classification Search
CPC ......... H01F 1/00054; A61K 6/17; A61K 6/16; A61K 6/71; A61K 6/831; A61K 6/84; A61K 6/884; C01P 2006/41; C01P 2004/02; C01P 2004/64; C01P 2004/80; C01P 2004/84; C09C 1/0051; C09C 2200/1004; C09C 2200/1054; C09C 2200/308; C09C 2200/302; C09C 2200/303; C09C 2210/00

See application file for complete search history.

(56) References Cited

U.S. PATENT DOCUMENTS

| | | |
|---|---|---|
| 5,194,356 A | 3/1993 | Sacripante et al. |
| 5,427,767 A | 6/1995 | Kresse |
| 5,763,085 A * | 6/1998 | Atarashi .................. B22F 1/17 |
| | | 428/570 |
| 6,517,627 B1 | 2/2003 | Atarashi et al. |
| 9,617,534 B2 | 4/2017 | Hennig et al. |
| 9,668,946 B2 | 6/2017 | Moszner et al. |
| 9,721,705 B2 | 8/2017 | Choe et al. |
| 10,213,367 B2 | 2/2019 | Moszner et al. |
| 2014/0371341 A1 | 12/2014 | Moszner et al. |
| 2015/0147537 A1* | 5/2015 | Lee ........................ G06F 3/041 |
| | | 106/404 |
| 2018/0112076 A1* | 4/2018 | Huber ....................... C03C 1/04 |

FOREIGN PATENT DOCUMENTS

| | | |
|---|---|---|
| DE | 102015118816 A1 | 5/2017 |
| JP | H 06228604 A | 8/1994 |
| JP | 2000150218 A | 5/2000 |
| JP | 2003002658 A | 1/2003 |
| WO | 2010149150 A1 | 12/2010 |

OTHER PUBLICATIONS

Science all around us, BASF, Jan. 20, 2012.*
Braziulis, Erik, "Variolink Esthetic," 30 pages, Scientific Documentation, voclar Vivadent AG, Schaan, Liechtenstein, Sep. 2014 and Aug. 2018.

* cited by examiner

*Primary Examiner* — C Melissa Koslow (74) *Attorney, Agent, or Firm* — Ann M. Knab; Thad McMurray (57) ABSTRACT

The present invention relates to particles comprising a core, in particular a magnetic core, and a first coating of a first shell material, wherein a second coating of a second shell material is applied to the surface of the first coating facing away from the core, the second shell material is different from the first shell material and has a higher refractive index than the first shell material.

14 Claims, 7 Drawing Sheets
(2 of 7 Drawing Sheet(s) Filed in Color)

PARTICLES WITH IMPROVED COLOUR SHIELDING

CROSS-REFERENCE TO RELATED APPLICATIONS

This application claims priority to European patent application No. 18193477.9 filed on Sep. 10, 2018, the disclosure of which is incorporated herein by reference in its entirety.

TECHNICAL FIELD

The present invention relates to particles and the colour shielding thereof and in particular magnetic particles and the use thereof as filler for local heat generation and in particular as filler in dental materials, in particular for the preparation of adhesives and cements.

BACKGROUND

Magnetic particles and in particular magnetic nanoparticles, i.e. magnetic particles with a diameter of less than 300 nm, are of major interest due to their great potential for application in various fields such as, amongst others, catalysis, diagnostics, therapy, water treatment and data storage.

It is known to apply a coating to the particles to protect or stabilize the particles, e.g. against corrosion or agglomeration. A coating can also serve for the further functionalization or modification of the particles for further different applications.

For example, DE 10 2015 118 816 describes anisotropic iron oxide nanoparticles with a diameter of from 3 to 50 nm which are embedded into a silicate matrix and can be used as a component of security features, e.g. in documents or security papers. Nanocrystalline magnetic iron oxide particles which are surrounded by a shell material of natural or synthetic glycosaminoglycans, and the use thereof in medical diagnostics and therapy, are disclosed, for example, in DE 41 17 782 and corresponding U.S. Pat. No. 5,427,767, which is hereby incorporated by reference. Furthermore, EP 1 894 214 and corresponding US2010063263, US2015191718, US2017159043, US2019241885, and US961753, which U.S. publications and patents are hereby incorporated by reference in their entirety, describe a method for the production of silica-coated magnetic particles and the use thereof for the purification of nucleic acids from biological body samples.

It is furthermore known that magnetic particles can generally be used for local indirect heat generation. Thus, magnetic particles which are exposed to an alternating electromagnetic field can convert some of the energy of the alternating field into heat due to hysteresis and relaxation processes. The thermal treatment of tumour cells with remotely controlled inductive heating in the radiofrequency range, wherein the tumour cells are killed by the local effect of heat, represents an example of an application utilizing this effect.

The inductive heat generation capability of magnetic particles can also be used for the debonding of adhesive bonds on demand, so-called debonding-on-demand (DoD). In this context, the debonding of adhesive bonds can be achieved on demand by significantly reducing the strength of the adhesive bond layer by heating.

Thus, for example, WO 2013/034777 and corresponding US 2014329929, US 2014371341, U.S. Pat. Nos. 9,320,686, and 9,668,946, which US publications and patents are hereby incorporated by reference, propose the incorporation of ferromagnetic nanoparticles into dental materials, in particular adhesives and cements, in order to achieve an inductive heating of the dental material by the action of an alternating magnetic field. In the dental field, the debonding of adhesive bonds is important among other things in orthodontics, where brackets which are bonded to the tooth surface to correct malocclusions must be removed again after successful correction without damaging the tooth enamel. Moreover, in the case of repair or complete replacement of high-strength ceramic restorations or crowns which are laborious to remove mechanically, cement bonds that can be easily softened or separated would be advantageous.

However, a disadvantage of the use of magnetic particles in dental materials is often the dark colour of the magnetic particles. In particular, particles the diameter of which is large enough to provide customized magnetic properties for debonding-on-demand applications, such as e.g. an adequate coercivity, are visible to the human eye as a grey or dark spot in the dental material, or lead overall to a darkening of the dental material, which is undesired for aesthetic reasons.

It is indeed known to lighten the colour of magnetic particles through the addition of white pigments. For example, JP 2000/150218 describes the coating of magnetic cores with white pigments. JP 2003/002658 discloses white magnetic particles which are obtained by applying fine magnetic iron oxide particles to the surface of white $TiO_2$ cores. Furthermore, U.S. Pat. No. 5,194,356, which is hereby incorporated by reference, and WO 2010/149150 each describe the incorporation of magnetic particles and white pigments into a polymer matrix.

However, the present inventors have found that magnetic particles that are lightened with pigments, such as e.g. iron oxide particles with a silica-containing coating, and have a nearly neutral colour with only a slightly light-grey shade in air, exhibit a considerably darker colour when embedded in a dental medium, such as dental cement.

SUMMARY

The object of the invention is thus to provide particles with improved colour shielding. In particular, the object of the invention is to provide magnetic particles which have adequate magnetic properties for local, induced heat generation and are thus suitable for debonding-on-demand applications in the dental field, and at the same time have an aesthetic appearance, i.e. a colour that is as neutral as possible, in adhesive media such as dental adhesives or dental cements.

BRIEF DESCRIPTION OF THE DRAWINGS

The patent or application file contains at least one drawing executed in color. Copies of this patent or patent application publication with color drawings will be provided by the Office upon request and payment of the necessary fee. Further advantages, details and features may be taken from the following description of several exemplary embodiments in conjunction with the drawings, in which.

DETAILED DESCRIPTION

The object of the invention is achieved by particles which comprise a core and a first coating of a first shell material, wherein a second coating of a second shell material is applied to the surface of the first coating facing away from the core, wherein the second shell material is different from the first shell material and has a higher refractive index than the first shell material. In particular, the object is achieved according to the invention by magnetic particles which comprise a magnetic core and a first coating of a first shell material, wherein a second coating of a second shell material is applied to the surface of the first coating facing away from the core, wherein the second shell material is different from the first shell material and has a higher refractive index than the first shell material. Surprisingly, it has been found that an undesirable colour of the particle core, in particular the undesirable dark colour of magnetic particles, not only in air but also in adhesive media such as dental adhesives or dental cements, can be effectively shielded through the combination according to the invention of a first and second coating. The magnetic particles according to the invention are thus characterized not only by adequate magnetic properties for local, induced heat generation, but in particular also by excellent optical properties when embedded in adhesive media.

Without wishing to be bound to any one theory, it is assumed that an undesirable dark colour, i.e. absorption of incident light by the core material, is minimized in the case of particles according to the invention in that incident light is deflected away from the core by the ratio according to the invention of the refractive indices of the shell materials and the double shell thus leads to a focusing of the incident light outside the core. The coating according to the invention of magnetic cores can thus lead to an effective colour shielding even when the particles are embedded in media with a refractive index of greater than 1.0, such as e.g. from 1.4 to 1.5, as usually occurs in the case of adhesive media in the dental field.

In order to achieve the desired colour shielding as effectively as possible, in one embodiment both the first and the second coating are formed as a continuous coating. Particularly preferably, the surface of the core is completely covered by the first shell material and the surface of the first coating facing away from the core is completely covered by the second shell material.

It is furthermore preferred that both the first and the second coating are formed substantially even, i.e. that both the thickness of the first coating and the thickness of the second coating is substantially constant over its entire extent.

In a preferred embodiment in which the desired colour shielding of the core is particularly effective, the ratio of the refractive index of the second shell material to the refractive index of the first shell material is from 1.1 to 2.6, preferably 1.4 to 2.0, particularly preferably 1.6 to 1.8.

In one embodiment, the first shell material has a refractive index of from 1.1 to 2.5, preferably 1.2 to 1.9, particularly preferably 1.3 to 1.7. Furthermore, the second shell material preferably has a refractive index of from 1.7 to 3.1, in particular 2.1 to 3.1, particularly preferably 2.5 to 3.1.

Unless otherwise indicated, the specification of the refractive index of the first and second shell material in the present application refers to the material constant of the respective material at a wavelength of 589 nm (sodium D line) and a temperature of 25° C.

In a further embodiment, it is preferred that the ratio of the thickness of the second coating to the thickness of the first coating is from 0.1 to 2.5, preferably 0.5 to 2.0, particularly preferably 1.0 to 2.0. In particular, the thickness of the first coating is preferably from 50 to 1000 nm, particularly preferably 100 to 600 nm. Furthermore, the thickness of the second coating is preferably from 50 to 1000 nm, particularly preferably 100 to 600 nm.

In this context, the thickness of the first and second coatings is determined with the aid of scanning electron microscopy (SEM), wherein the number-average diameter of the particles without a coating to be determined is subtracted from the number-average diameter of the particles with a coating to be determined. The thickness of the coating is equal to half this difference in the diameters, i.e. the thickness of the coating corresponds to the difference in the corresponding radii.

Furthermore, it is preferred that the ratio of the thickness of the second coating to the radius of the first coating is from 0.1 to 2.5, 1.0 to 2.0 or 0.1 to 1, preferably 0.2 to 0.8, particularly preferably 0.28 to 0.8.

In this context, the radius of the first coating is determined in particular with the aid of scanning electron microscopy (SEM), wherein the core coated with the first coating preferably has a substantially spherical form and the radius of the first coating is thus half the number-average diameter of the cores provided with the first coating.

Particularly preferably, the second shell material is selected from the group consisting of TiO$_2$, ZrO$_2$, ZnS, Al$_2$O$_3$, poly(pentabromophenyl methacrylate) and mixtures thereof. Furthermore, the first shell material is particularly preferably selected from the group consisting of SiO$_2$, SiO$_2$ acrylate, polystyrene, polymethyl methacrylate, polyvinyl alcohol, polyalkyl acrylate, polycarbonate, MgF$_2$, fluorinated polymer, Al$_2$O$_3$, ZZnO and mixtures thereof. The term "SiO$_2$ acrylate" here denotes polymers of 3-(trimethoxysilyl)propyl methacrylate (TPM). Examples of suitable fluorinated polymers comprise fluorinated acrylates with a low refractive index, such as poly(1,1,1,3,3,3-hexafluoroisopropyl acrylate), poly(2,2,3,3,4,4,4-heptafluorobutyl acrylates), poly(2,2,3,3,4,4,4-heptafluorobutyl methacrylate), poly(2,2,3,3,3-pentafluoropropyl acrylate), poly(1,1,1,3,3,3-hexafluoroisopropyl methacrylate), poly(2,2,3,4,4,4-hexafluorobutyl acrylate), poly(2,2,3,4,4,4-hexafluorobutyl methacrylate), poly(2,2,3,3,3-pentafluoropropyl methacrylate), poly(2,2,2-trifluoroethyl acrylate), poly(2,2,3,3-tetrafluoropropyl acrylate), poly(2,2,3,3-tetrafluoropropyl methacrylate) and poly(2,2,2-trifluoroethyl methacrylate).

Magnetic particles in which the first shell material is $SiO_2$ and the second shell material is $TiO_2$ are particularly preferred. Furthermore, the $SiO_2$ of the first shell material is preferably porous, and in particular microporous, $SiO_2$.

The core of the particles according to the invention is preferably not completely transparent to light, but opaque. In particular, the core has an opaqueness or otherwise undesirable colour in the range of visible light, which gives rise to the desire for a colour shielding.

As mentioned above, in a particularly preferred embodiment the core of the particles according to the invention is magnetic, with the result that the particles according to the invention represent magnetic particles. The magnetic core of such magnetic particles according to the invention can be heated inductively. In particular, the core transforms electromagnetic energy into thermal energy when it is exposed to an alternating electromagnetic field. In one embodiment, the magnetic core is ferromagnetic or ferrimagnetic.

In a further embodiment, the magnetic core comprises a material selected from the group consisting of (i) iron oxide, in particular haematite ($Fe_2O_3$) and/or magnetite ($Fe_3O_4$), (ii) ferrites of the general formula $MeO.Fe_2O_3$, wherein Me is selected from the group consisting of Ni, Zn, Mn, Co, Cu, Mg, Cd, Ba and Sr, (iii) mixed ferrites of the general formula $Me_yFe_{3-y}O_4$, wherein Me is selected from the group consisting of Ni, Zn, Mn, Co, Cu, Mg, Cd, Ba and Sr, and y is between 0 and 1, (iv) metals and metal alloys from the group consisting of Co, Ni, Fe, Nd, AlNiCo, FeNi, SmCo and NdFeB and (v) further oxides such as $CrO_2$. The magnetic core is preferably selected from the group consisting of $Fe_3O_4$, $CoFe_2O_4$ and $Co_yFe_{3-y}O_4$, wherein y is between 0 and 0.3. The magnetic core particularly preferably consists of $Fe_3O_4$.

The magnetic core can be single-domain or multi-domain. A magnetic particle according to the invention preferably contains a multi-domain core. Furthermore, the magnetic core preferably has an average diameter of from 10 to 1000 nm, in particular 25 to 700 nm, particularly preferably 100 to 500 nm, wherein the average diameter is the number-average diameter determined by means of transmission electron microscopy (TEM).

Suitable magnetic cores are available, for example, under the trade name Bayoxide® from Lanxess.

The magnetic core can be any shape, including but not limited to, spherical, cube-shaped or rod-shaped. The core preferably has a substantially spherical or cube-shaped form.

Correspondingly, the coated particle according to the invention also has a spherical, cube-shaped or rod-shaped and preferably a substantially spherical form. In a preferred embodiment, the particle according to the invention has an average diameter of from 10 to 2000 nm, preferably 25 to 1500 nm, particularly preferably 300 to 1000 nm, wherein the average diameter is the number-average diameter which is particularly preferably determined by means of SEM, wherein a determination by means of TEM is also possible for smaller particles, such as particles with a diameter of e.g. less than 400 nm.

The particles according to the invention are easy to prepare. For example, the particles, and in particular the magnetic particles according to the invention, can be prepared by a process in which (a) cores, in particular magnetic cores, are dispersed,
(b) a precursor compound of the first shell material is added to the dispersion obtained in step (a) and the mixture obtained is exposed to conditions which are sufficient to deposit the first shell material as first coating on the cores,
(c) a dispersion of the cores coated with the first shell material is provided and
(d) a precursor compound of the second shell material is added to the dispersion obtained in step (c) and the mixture obtained is exposed to conditions which are sufficient to deposit the second shell material as second coating on the first coating.

In step (a) a dispersion of cores, in particular magnetic cores, is provided. The cores are preferably dispersed in a suitable solvent with the aid of ultrasound or a suitable stirrer. An alcoholic solvent, in particular ethanol, is preferably used.

In step (b) the cores are coated with the first shell material. For this a precursor compound of the first shell material is added to the dispersion of the cores. For example, organometallic precursor compounds, such as alkoxy metal compounds, are suitable as precursor compound. In the case of $SiO_2$ as first shell material, an alkoxysilane, in particular tetraethyl orthosilicate, is preferably added as precursor material. The deposition of the first shell material can be promoted through the addition of a catalyst, such as e.g. acids or bases. For example in the case of alkoxysilanes as precursor material, a base such as $NH_4OH$ can be added as catalyst. The catalyst can be added before the addition, at the same time as the addition or after the addition of the precursor compound. Particularly preferably, $NH_4OH$ is added before the addition of the $SiO_2$ precursor material.

The coating in step (b) is preferably effected at room temperature. In addition, it is preferred that the reaction mixture in step (b) is dispersed further during the coating process, e.g. by means of ultrasound or intensive stirring. The particles provided with the first coating can optionally be separated off, e.g. with the aid of magnetic processes, and optionally characterized.

Then in step (c) a dispersion of the singly coated cores is provided. Also the coated cores are also preferably dispersed in a suitable solvent, such as an alcoholic solvent, with the aid of ultrasound or a suitable stirrer. In the case of $SiO_2$ as first shell material, the singly coated particles are preferably dispersed in a mixture of THF and ethanol.

In step (d) a precursor compound of the second shell material is added to the dispersion. Suitable precursor compounds comprise, for example, organometallic precursor compounds, such as alkoxy metal compounds. In the case of $TiO_2$ as second shell material, a titanate, in particular tetrabutyl orthotitanate, is preferably added as precursor material. The deposition of the second shell material can be promoted through the addition of a catalyst, such as e.g. acids or bases. For example in the case of titanates as precursor material, a base such as $NH_4OH$ can be added as catalyst. The catalyst can be added before the addition, at the same time as the addition or after the addition of the precursor compound. Particularly preferably, $NH_4OH$ is added after the addition of the $TiO_2$ precursor material, in particular 30 to 120 min and preferably 40 to 90 min after the addition of the precursor material. It has been found that the porosity of the second coating can be reduced through such an addition.

The coating in step (d) is preferably carried out at a precursor concentration of from 0.10 to 0.40 mol/l, in particular 0.15 to 0.30 mol/l, particularly preferably 0.17 to 0.29 mol/l. It is also preferred that the catalyst concentration is from 0.005 to 0.03 mol/l, in particular 0.01 to 0.015 mol/l. It has been found that, in particular when titanates such as tetrabutyl orthotitanate are used as precursor compound, and a base such as $NH_4OH$ is used as catalyst, the above preferred concentration ranges result in an even and thick coating with reduced porosity and crack formation.

The magnetic particles according to the invention can be separated off after step (d), e.g. with the aid of magnetic processes, and optionally characterized.

The magnetic particles according to the invention can be used in particular as filler for local heat generation. In particular, because of the magnetic core, the magnetic particles according to the invention are able to generate heat locally when they are exposed to an alternating electromagnetic field. The locally generated heat can be used, for example, to debond adhesive compounds on demand. The magnetic particles according to the invention can thus be used particularly well as filler with debonding-on-demand properties.

Thus a subject of the invention is also the use of the magnetic particles according to the invention as filler for local heat generation and as filler in adhesive materials, in particular adhesive materials with debonding-on-demand properties.

In addition, the magnetic particles according to the invention also meet the aesthetic demands placed on dental materials due to the effective colour shielding of the magnetic cores which are in themselves dark and opaque. Thus the magnetic particles according to the invention can in particular also be used as filler in dental materials. Therefore, the present invention also relates to the use of the magnetic particles according to the invention as filler in dental materials, in particular adhesives and cements.

The dental adhesives or dental cements can be used in particular for the reversible fixing of, for example, brackets, crowns or veneers. In this context, first of all the formation of a bond is preferably effected by curing of materials (adhesive or cement) based on e.g. one or more thermolabile polymerizable compounds. For the debonding, the bonded parts have to be briefly heated to a temperature which is above the temperature at which the cleavage of the thermolabile bonds begins. In this context, a targeted supply of energy by means of inductive heating of the magnetic particles according to the invention can be achieved by the action of an alternating magnetic field.

Thus the invention also relates to a polymerizable dental material which may be at least one radically polymerizable compound. The polymerizable dental material contains magnetic particles according to the invention in addition to at least one radically polymerizable compound. The polymerizable compound is preferably a monomer with debonding-on-demand properties, i.e. a monomer which leads to the formation of an adhesive layer the strength of which can be considerably reduced, e.g. by heating. Such monomers with debonding-on-demand properties are described, for example, in WO 2013/034777 and WO 2016/005540 and corresponding U.S. Ser. No. 10/213,367 and US 2017156993, of which US publications are hereby incorporated by reference.

As described above, the double-shell coating of the magnetic particles according to the invention surprisingly results in the particles having a lighter colour not only in air, but also in dental media such as e.g. dental adhesives and dental cements. Therefore, the present invention also relates to the use of a first coating of a first shell material and a second coating of a second shell material for the colour masking of particles, in particular magnetic particles, wherein the first coating is applied to the particle to be masked and the second coating is applied to the surface of the first coating facing away from the particle, and the second shell material is different from the first shell material and has a higher refractive index than the first shell material.

The invention is explained in more detail below by means of embodiment examples.

EMBODIMENT EXAMPLES

Example 1

Preparation of $Fe_3O_4$ Cores with Double-Shell Coating

In this example the preparation of $Fe_3O_4$ cores with a double-shell coating is described, wherein the inner coating is $SiO_2$ and the outer coating is $TiO_2$. Particles coated in this way are also referred to below as $Fe_3O_4@SiO_2@TiO_2$. The preparation was effected in two steps. In the first step, magnetic $Fe_3O_4$ particles were coated with $SiO_2$. The $Fe_3O_4@SiO_2$ particles obtained were subsequently coated with $TiO_2$.

i) Preparation of $Fe_3O_4@SiO_2$:

Magnetic $Fe_3O_4$ particles (cube-shaped; number-average diameter according to TEM of 226±77 nm) were dispersed in ethanol (EtOH) for 5 min in a 500-ml three-neck round-bottomed flask with the aid of an ultrasonic bath. Ammonia ($NH_4OH$, 25%) and water were added thereto and dispersed for a further 5 min. Tetraethyl orthosilicate (TEOS) was diluted in 100 ml EtOH and added dropwise to the particle dispersion under protective gas ($N_2$) at room temperature. After the addition of TEOS, the particle dispersion was further dispersed for 1 h in an ultrasonic bath. The particles were then purified with EtOH, magnetically separated, dried under vacuum, and the magnetic content was determined with the aid of Vibrating Sample Magnetometry (VSM).

The amounts of magnetic particles, TEOS, EtOH and $NH_4OH$ used for the preparation of $Fe_3O_4@SiO_2$ particles as well as the magnetic content $\mu_{mag}$ of the $Fe_3O_4@SiO_2$ particles obtained are given in the following table:

| $Fe_3O_4$ particles [mg] | TEOS [ml] | TEOS [mmol] | EtOH [ml] | Drip rate [ml · h$^{-1}$] | $NH_4OH$ [ml] | $\mu_{mag}$ [m %] |
|---|---|---|---|---|---|---|
| 120 | 5 | 22.6 | 100 | 26 | 15 | 15.2 |

Figure 1:
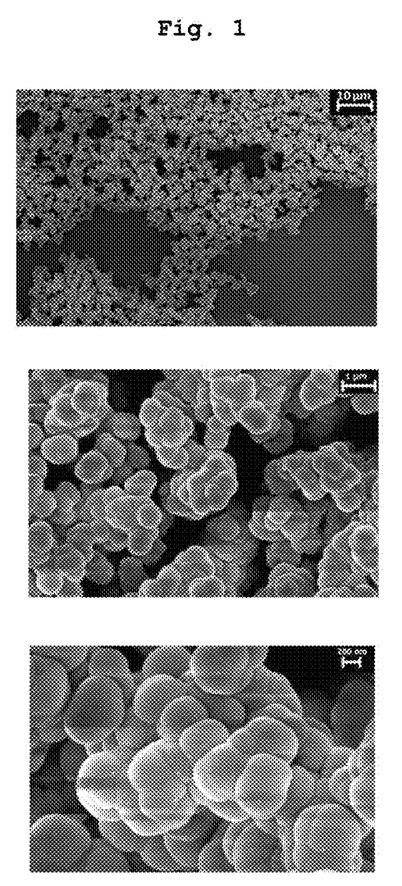
FIG. 1 shows SEM micrographs of prepared $Fe_3O_4@SiO_2$ particles.

FIG. 1 shows SEM micrographs of the prepared $Fe_3O_4@SiO_2$ particles. The particles have a virtually spherical geometry with an average diameter of 699±112 nm determined by SEM.

ii) Preparation of $Fe_3O_4@SiO_2@TiO_2$:

The $Fe_3O_4@SiO_2$ particles from the previous step were dispersed in a THF/EtOH mixture (1:4 v/v) for 5 min in a 100-ml three-neck round-bottomed flask with the aid of an ultrasonic bath. The three-neck round-bottomed flask was connected during this time to a calibrated precision glass stirrer. Tetrabutyl orthotitanate (TBOT) was diluted in 20 ml EtOH and slowly added dropwise (5.0 ml/h) to the particle dispersion under protective gas ($N_2$) at room temperature. Ammonia ($NH_4OH$, 25%) and water were added thereto after a specific amount of time. After the addition of TBOT, the particle dispersion was further stirred for 1 h. The particles were then purified five times with 15 ml EtOH each time, magnetically separated, dried under vacuum, and the magnetic content was determined with the aid of VSM measurements.

The amounts of $Fe_3O_4@SiO_2$ particles, TBOT, EtOH, THF, water and $NH_4OH$ used as well as the magnetic content $\mu_{mag}$ of the $Fe_3O_4@SiO_2$ particles obtained are given in the following table:

| Ex. | Fe$_3$O$_4$@ SiO$_2$ [mg] | TBOT [ml] | THF/ EtOH [ml] | H$_2$O$^a$ [ml] | NH$_4$OH [µl] | Time of addition of NH$_4$OH$^b$ [h] | µ$_{mag}$ [m %] |
|---|---|---|---|---|---|---|---|
| a) | 24 | 0.5 | 25 | 0.5 | 0.1 | 1 | 9.8 |
| b) | 24 | 1 | 25 | 0.5 | 0.1 | 1 | 6.6 |
| c) | 24 | 4 | 25 | 0.5 | 0.1 | 1 | 5.0 |
| d) | 24 | 3 | 25 | 0.25 | 0.05 | 1 | 2.0 |
| e) | 24 | 4 | 25 | 0.25 | 0.05 | 1 | 1.6 |
| f) | 24 | 2 | 25 | 0.25 | 0 | 0 | 1.9 |
| g) | 24 | 2 | 25 | 0.25 | 0.05 | 1 | 7.7 |
| h) | 24 | 2 | 25 | 0.5 | 0.1 | 1 | 4.9 |
| i) | 12 | 1 | 12.5 | 0.25 | 0.025 | 1 | 2.4 |
| j) | 12 | 1 | 12.5 | 0.25 | 0.05 | 1 | 6.2 |
| k) | 12 | 1 | 12.5 | 0.25 | 0.1 | 1 | 4.1 |

Figure 2A:
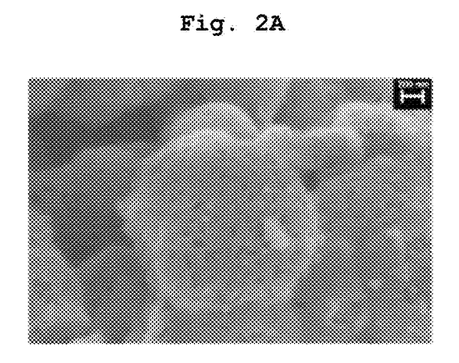
FIG. 2A shows an SEM micrograph of the particles obtained in Example 2f.
Figure 2B:
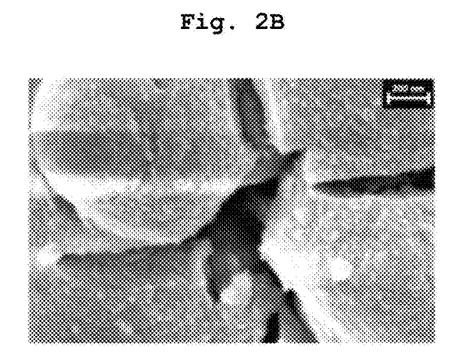
FIG. 2B shows an SEM micrograph of the particles obtained in Example 2h.
Figure 2C:
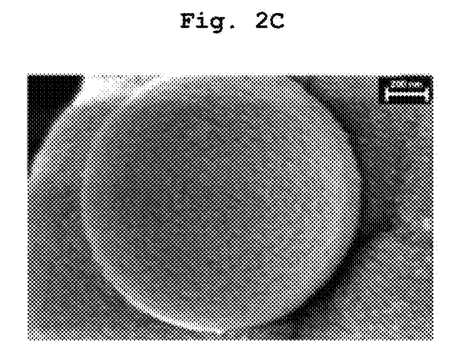
FIG. 2C shows an SEM micrograph of the particles obtained in Example 2d.

$^a$H$_2$O was added one hour after the addition of NH$_4$OH.
$^b$Time of the addition of NH$_4$OH after the start of the addition of TBOT FIG. 2 shows SEM micrographs of the prepared Fe$_3$O$_4$@SiO$_2$@TiO$_2$ particles, wherein FIG. 2A shows the particles obtained in Example 2 f), FIG. 2B shows the particles obtained in Example 2 h) and FIG. 2C shows the particles obtained in Example 2 d). It can be seen that carrying out the second coating reaction without the addition of base resulted in a TiO$_2$ coating with a porous morphology on the SiO$_2$ surface (FIG. 2A). The results also show that the formation of free TiO$_2$ particles was able to be reduced and the porosity of the coated particles minimized when the base catalyst was first added 60 min after the start of the addition of the TiO$_2$ precursor material (FIG. 2C).

Figure 3:
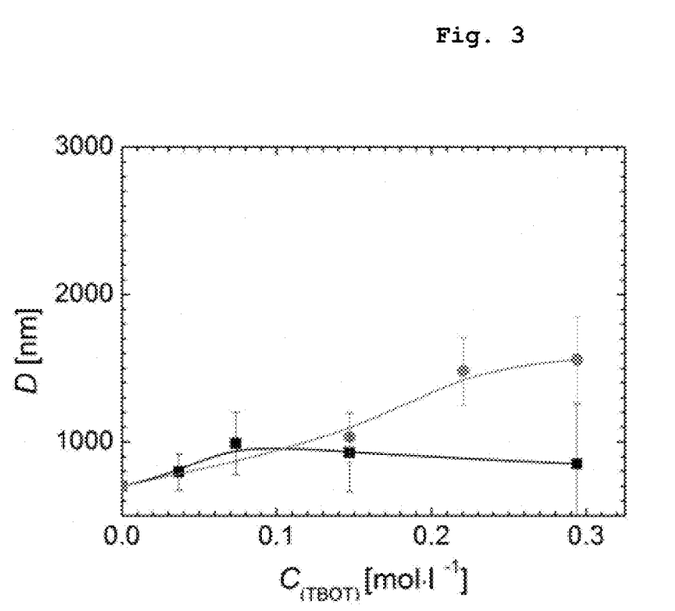
FIG. 3 shows the influence of the TBOT concentration on the particle diameter for two different base concentrations.
Figure 4:
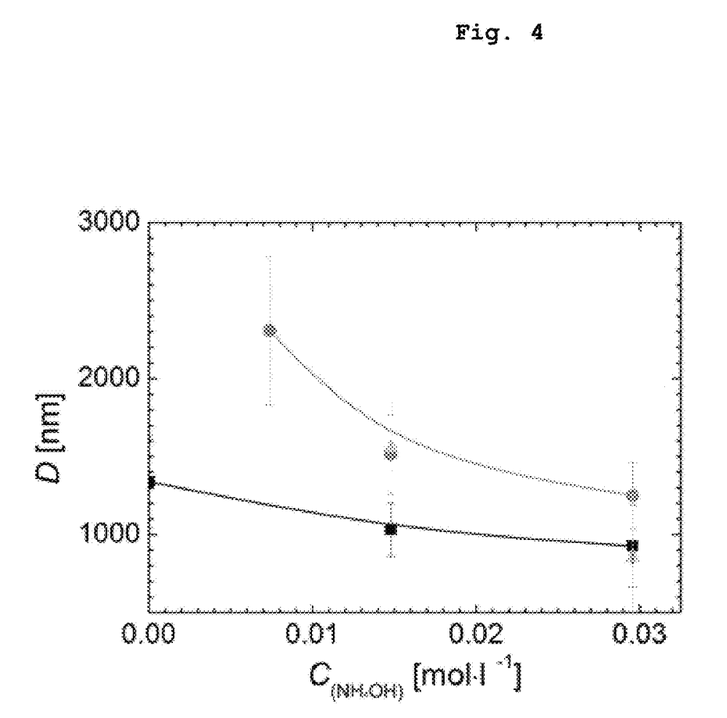
FIG. 4 shows the influence of the NH$_4$OH concentration on the particle diameter determined by means of SEM for different TBOT concentrations.

FIG. 3 shows the influence of the TBOT concentration on the particle diameter for two different base concentrations (circles: 0.014 mol/l NH$_4$OH; squares: 0.029 mol/l). FIG. 4 shows the influence of the NH$_4$OH concentration on the particle diameter determined by means of SEM for different TBOT concentrations (circles: 0.07 mol/l TBOT; squares: 0.17 TBOT; triangles: 0.29 mol/l). Both in FIG. 3 and in FIG. 4 the base concentration relates to the final volume of the reaction mixture. The continuous lines in both figures serve for illustration. An increasing TBOT concentration resulted in larger diameters at a moderate base concentration (0.014 mol/l), whereas an increase in the base concentration resulted in smaller particle diameters. An increasing TBOT concentration at a high base concentration in the reaction mixture can result in a formation of free TiO$_2$ particles. A high NH$_4$OH concentration (e.g. 0.029 mol/l) can result in the formation of cracks in the prepared particles (see also FIG. 2B) due to the rapid hydrolysis of the TBOT radicals on the surface of the particles. The best coating results were obtained (see FIG. 2C) at TBOT concentrations of 0.17 mol/l-0.29 mol/l and base concentrations of 0.01 mol/l-0.015 mol/l. The magnetic particles prepared have a colour-neutral visual appearance compared with Fe$_3$O$_4$@TiO$_2$ particles, i.e. Fe$_3$O$_4$ particles with a single TiO$_2$ coating.

Figure 5:
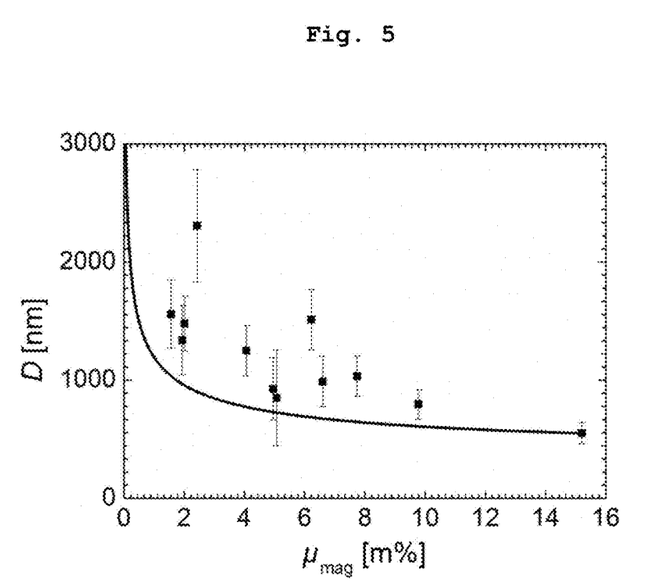
FIG. 5 shows the dependence of the particle diameter on the magnetic content $\mu_{mag}$ of the Fe$_3$O$_4$@SiO$_2$@TiO$_2$ particles.

FIG. 5 shows the dependence of the particle diameter on the magnetic content µ$_{mag}$ of the Fe$_3$O$_4$@SiO$_2$@TiO$_2$ particles. It can be seen that the magnetic content of the Fe$_3$O$_4$@SiO$_2$@TiO$_2$ particles is less than 15.2%, which is the magnetic content of the Fe$_3$O$_4$@SiO$_2$ particles used as starting material, and the particle size generally increases as the magnetic content decreases. A successful coating can thus be assumed to have taken place. The continuous line represents the theoretical relationship between the magnetic content and the particle diameter, which is described by the following equation:

$$\mu_{mag} = \frac{m_{(core)}}{m_{(core)} + m_{(shell)}} = \frac{m_{(core)}}{m_{(total)}} = \frac{\rho_{(core)} \cdot v_{(core)}}{\rho_{(total)} \cdot v_{(total)}} = \frac{\rho_{(core)} \cdot d_m^3}{\rho_{(total)} \cdot D^3},$$

wherein p: density, m: mass, d$_m$: diameter of core and D: diameter of core-shell particles, wherein, for this case, the Fe$_3$O$_4$@SiO$_2$ particles are to be regarded as core particles and the result of the above equation are multiplied by p$_{mag}$ in percent of Fe$_3$O$_4$@SiO$_2$ core particles (15.2%) in order to adapt the equation to the double-shell architecture.

Example 2

Embedding of Fe$_3$O$_4$@SiO$_2$@TiO$_2$ in Dental Cement

Fe$_3$O$_4$@SiO$_2$@TiO$_2$ particles were embedded in dental cements in order to obtain magnetic dental cement composites. Dual-curing dental cement DC and LC (Variolink Esthetic DC/LC) was used as dental cement. For the preparation of the composites, approximately 0.25 g dental cement (LC) was dissolved or dispersed in 2 ml EtOH in darkened rolled rim glassware with the aid of an ultrasonic bath. Fe$_3$O$_4$@SiO$_2$@TiO$_2$ particles were added thereto and further dispersed at 70° C. for 30 min with the aid of an ultrasonic bath. The mixture was dried in a drying oven. The magnetic content of the composites was then determined with the aid of VSM measurements.

The amounts of Fe$_3$O$_4$@SiO$_2$@TiO$_2$ particles and dental cement used as well as the magnetic content µ$_{mag}$ of the particles used and of the composite obtained are given in the following table:

| Ex. | Fe$_3$O$_4$@SiO$_2$@TiO$_2$ particles [mg] | Dental cement [mg] | µ$_{mag}$ particles [m %] | µ$_{mag}$ composite [m %] |
|---|---|---|---|---|
| a) | 2.7 | 250 | 1.6 | 0.02 |
| b) | 7.0 | 255 | 1.6 | 0.04 |
| c) | 13.7 | 255 | 1.6 | 0.08 |
| d) | 27.0 | 249 | 1.6 | 0.15 |
| e) | 3.75 | 249 | 2.0 | 0.02 |
| f) | 17.4 | 251 | 2.0 | 0.13 |
| g) | 2.7 | 250 | 7.7 | 0.15 |

For the test pieces investigated in Example 3, the low-viscosity composite was placed between two specimen slides, each with a metal disc with a thickness of 300 µm as spacer on each side, before the curing, with the result that test pieces with a thickness of approximately 300 µm were obtained. The curing was effected in daylight for 6 hours.

Example 3

Optical Properties of Fe$_3$O$_4$@SiO$_2$@TiO$_2$ in Dental Cement

The composites prepared according to Example 2 were investigated with regard to their visual appearance. For this, in each case a photograph was taken of the composites against a black/white background.

Figure 6:
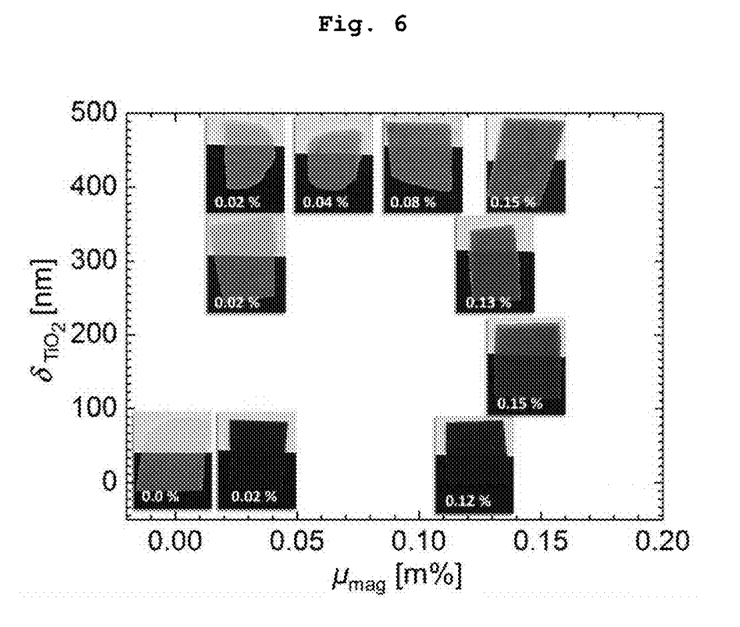
FIG. 6 shows a diagram with the results obtained of the magnetic content $\mu_{mag}$ of the composite plotted against the layer thickness of the outer shell.

FIG. 6 shows a diagram with the results obtained. Here, the magnetic content µ$_{mag}$ of the composite is plotted against the layer thickness of the outer shell δ$_{TiO2}$ of the Fe$_3$O$_4$@SiO$_2$@TiO$_2$ particles, wherein the TiO$_2$ layer thickness δ$_{TiO2}$ is the difference between the diameter of the double shell-coated particles Fe$_3$O$_4$@SiO$_2$@TiO$_2$ and the diameter of the singly coated particles Fe$_3$O$_4$@SiO$_2$. Here, the position of the photograph in the diagram approximately represents the corresponding coordinates of magnetic content of the composite—and thus the particle content of the composite—and the shell thickness of the particles.

In addition to the seven samples from Example 2, the photographs of three samples which do not contain any Fe$_3$O$_4$@SiO$_2$@TiO$_2$ particles (layer thickness of the outer shell δ$_{TiO2}$=0 nm) are furthermore represented in FIG. 6. Of these three samples, one has no magnetic particles at all ($\mu_{mag}$=0 m %) and the other two contain different amounts of $Fe_3O_4$@$SiO_2$ particles, in order to produce composites with $\mu_{mag}$=0.02 m % and 0.12 m %.

It can be seen from FIG. 6 that the increase in the magnetic content generally results in opaque and darker composites. The magnetic composites without a $TiO_2$ shell have a very dark colour, even with a magnetic content of only 0.02 m %. In contrast, the provision of a $TiO_2$ shell around the $Fe_3O_4$@$SiO_2$ particles leads to an effective colour shielding of the magnetic core of the magnetic particles. By increasing the $TiO_2$ layer thickness the colour shielding of the magnetic core can be further improved, with the result that composites with lighter colours are obtained.

Comparison Example 1

Preparation of $Fe_3O_4$ Cores with a Single Coating

In this example, the preparation of $Fe_3O_4$ cores with a coating of polymerized 3-(trimethoxysilyl)propyl methacrylate (TPM), $ZrO_2$ or $TiO_2$ is described. Particles coated in this way are also referred to below as $Fe_3O_4$@$SiO_2$ acrylate, $Fe_3O_4$@$ZrO_2$ and $Fe_3O_4$@$TiO_2$, respectively.

i) Preparation of $Fe_3O_4$@$SiO_2$ acrylate:

Magnetic $Fe_3O_4$ particles (cube-shaped; number-average diameter according to TEM of 138±31 nm) were placed in a 500-ml three-neck round-bottomed flask. THF was added thereto and the mixture was dispersed in an ultrasonic bath (100%, 37 kHz) for 10 min. EtOH was then added thereto and the mixture was dispersed in an ultrasonic bath (100%, 37 kHz) for 5 min. Water was then added thereto and the mixture was dispersed in an ultrasonic bath (100%, 37 kHz) for a further 5 min. Ammonia solution (25%) was added thereto and the mixture was dispersed in an ultrasonic bath (100%, 37 kHz) for 5 min. The three-neck round-bottomed flask was then connected to a calibrated precision glass stirrer (200 rpm) with a polytetrafluoroethylene stirring blade. TPM was added dropwise thereto under protective gas ($N_2$) and the mixture was stirred for 1 h. The polymerization of the acrylate radicals on the binary monomer was carried out with the aid of ATRP (Atom Transfer Radical Polymerization). The particle dispersion was flushed with argon for 20 min. The catalyst Cu(I)Br was then added thereto and flushed with argon for a further 20 min. The ligand PMDETA (N,N,N',N',N''-pentamethyldiethylenetriamine) was added thereto for the formation of the catalyst-ligand complex. Stirring under argon at room temperature for 20 min was followed by the addition of the initiator MBrP (methyl 2-bromopropionate), wherein the molar ratio of TPM:Cu(I)Br:PMDETA:MBrP was 50:1:1:2. The polymerization was carried out under protective gas. After 3 h, the particles were washed five times with approx. 15 ml EtOH and magnetically separated using a 400-mT magnet, in order to separate off the free silica. The free magnetic particles were then magnetically separated using an approx. 100-mT magnet. The core-shell particles were finally dried under vacuum at 85° C. and the magnetic content was determined with the aid of VSM measurements.

| $Fe_3O_4$ particles [mg] | TPM [µl] | CuBr [mg] | THF [ml] | EtOH [ml] | $H_2O$ [ml] | $NH_4OH$ [ml] | $\mu_{mag}^a$ [m %] |
|---|---|---|---|---|---|---|---|
| 120 | 1200 | 15.8 | 60 | 60 | 240 | 4 | 2.5 |

$^a$measured using VSM ii) Preparation of $Fe_3O_4$@$ZrO_2$

Magnetic $Fe_3O_4$ particles (cube-shaped; number-average diameter according to TEM of 226±77 nm) were dispersed in 20 ml EtOH for 5 min in a 100-ml three-neck round-bottomed flask with an ultrasonic bath. Ammonia ($NH_4OH$, 25%) and 62.5 µl water were added thereto and dispersed for a further 5 min. The three-neck round-bottomed flask was connected during this time to a calibrated precision glass stirrer (200 rpm). The ultrasonic bath was removed, and zirconium tetrabutanolate (TBOZ) was added dropwise to the particle dispersion under protective gas ($N_2$) at room temperature with the aid of a syringe pump. After the addition of TBOZ, the particle dispersion was stirred for one hour. The particles were then purified five times with 15 ml EtOH and magnetically separated.

The amounts of $Fe_3O_4$ particles, TBOZ, EtOH, water and $NH_4OH$ used as well as the magnetic content $\mu_{mag}$ of the $ZrO_2$@$Fe_3O_4$ particles obtained are given in the following table:

| $Fe_3O_4$ particles [mg] | TBOZ [ml] | TBOZ [mmol] | Drip rate [ml · h$^{-1}$] | $H_2O$ [µl] | $NH_4OH$ [µl] | $\mu_{mag}^a$ [m %] |
|---|---|---|---|---|---|---|
| 24 | 4 | 11.8 | 5 | 62.5 | 12.5 | 3.8 |

$^a$measured by means of VSM iii) Preparation of $Fe_3O_4$@$TiO_2$

Magnetic $Fe_3O_4$ particles (cube-shaped; number-average diameter according to TEM of 226±77 nm) were dispersed in THF/EtOH (1:4 v/v) for 5 min in a 100-ml three-neck round-bottomed flask with an ultrasonic bath. Ammonia ($NH_4OH$, 25%) and 500 µl water were added thereto and dispersed for a further 5 min. TBOT diluted in 20 ml EtOH was added dropwise to the particle dispersion under protective gas ($N_2$) at room temperature with the aid of a syringe pump. After the addition of TBOT, the particle dispersion was stirred for one hour. The particles were then purified five times with approx. 15 ml EtOH each time, magnetically separated and dried under vacuum.

The amounts of $Fe_3O_4$ particles, TBOT, EtOH and $NH_4OH$ used as well as the magnetic content $\mu_{mag}$ of the $Fe_3O_4$@$TiO_2$ particles obtained are given in the following table:

| $Fe_3O_4$ particles [mg] | TBOT [ml] | TBOT [mmol] | EtOH/ THF [ml] | Drip rate [ml · h$^{-1}$] | $NH_4OH$ [µl] | $\mu_{mag}^a$ [m %] |
|---|---|---|---|---|---|---|
| 24 | 4 | 11.8 | 25 | 2.5 | 100 | 3.9 |

$^a$measured by means of VSM

Comparison Example 2

Optical Properties of $Fe_3O_4$ Cores with a Single Coating

Figure 7:
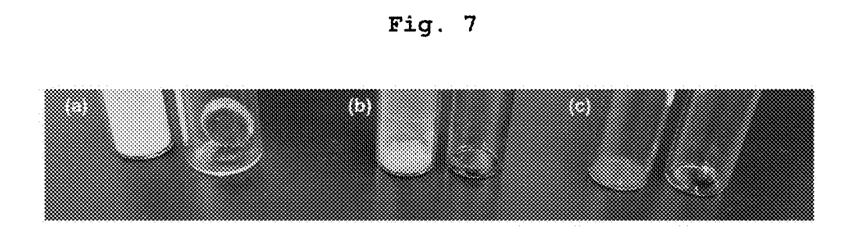
FIG. 7 shows the influence of the different shell materials on the optical properties of the magnetic particles.

The influence of the different shell materials on the optical properties of the magnetic particles is represented in FIG. 7. The photographs (a) show $Fe_3O_4$@$SiO_2$ acrylate particles in air (left) and $Fe_3O_4$@$SiO_2$ acrylate particles embedded in dental cement (right). The photographs (b) show $Fe_3O_4$@$ZrO_2$ particles in air (left) and $Fe_3O_4$@$ZrO_2$ particles embedded in dental cement (right). The photographs (c) show $Fe_3O_4$@$TiO_2$ particles in air (left) and $Fe_3O_4$@$TiO_2$ particles embedded in dental cement (right). The refractive index of the $SiO_2$ acrylate coating is approximately 1.5, whereas $ZrO_2$ has a refractive index of 2.18 and $TiO_2$ has a refractive index of 2.58.

Whereas $Fe_3O_4@SiO_2$ acrylate particles in air have a nearly neutral colour with a slightly light-grey shade, $Fe_3O_4@ZrO_2$ particles in air exhibited a grey colour and $Fe_3O_4@TiO_2$ particles in air exhibited an almost black colour.

A portion of the magnetic particles was then embedded in dental cement. For this, the coated magnetic particles with a concentration of 1 wt.-% were incorporated into dental cement (DC) and kept on a vortex shaker at maximum power for approximately 10 min until the dental cement became solid.

It can be seen from FIG. 7 that $Fe_3O_4@SiO_2$ acrylate exhibited a considerably darker colour in the dental cement matrix than in contact with air. This observation also applies to $Fe_3O_4@ZrO_2$ and $Fe_3O_4@TiO_2$. It should be taken into consideration here that the white edge which can be observed in the photographs of the dental cement samples is to be attributed to the shiny surface of the dental cement and thus to reflections and not to effects of the coating of the magnetic particles.

Figure 8:
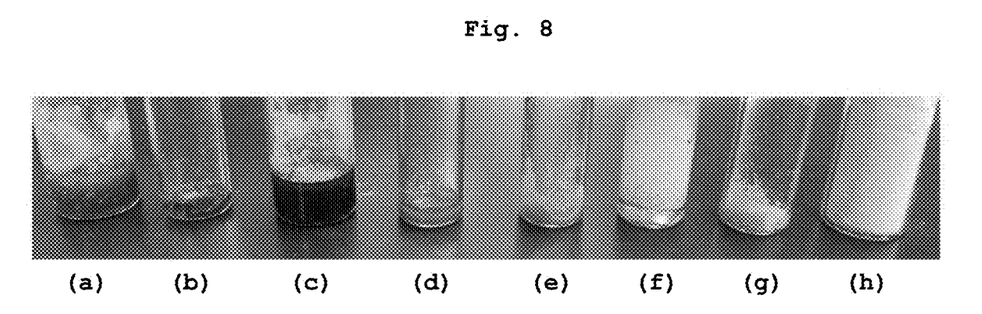
FIG. 8 shows a photograph of Fe$_3$O$_4$@SiO$_2$ acrylate particles which are dispersed in different media with different refractive indices.

The above observations show that the refractive index contrast between the shell material and the surrounding matrix plays a decisive role in visual appearance. This is also illustrated in FIG. 8 which shows a photograph of $Fe_3O_4@SiO_2$ particles which are dispersed in different media with different refractive indices, wherein the following media are used from left to right (in each case specifying their refractive index n): (a) polystyrene (n=1.58), (b) o-xylene (n=1.50), (c) polymethyl methacrylate (n=1.49), (d) 1,4-dioxane (n=0.42), (e) ethanol (n=1.37), (f) water (n=1.33), (g) trifluoroacetic acid (n=1.28) and (h) air (n=1.00). It can be seen that the colour of the dispersion becomes darker as the refractive index of the solvent increases, until a maximum appears to be reached at a refractive index of 1.49.

Example 4

In this example, the analysis of particles by means of VSM measurements, TEM measurements and SEM measurements is described.

VSM Measurements

The magnetic properties of the samples obtained herein were investigated with the aid of an EV7 Vibrating Sample Magnetometer (VSM) from ADE Magnetics. The magnetization of a sample was measured in dependence on the applied field, wherein the sample was vibrated perpendicular to a uniform magnetizing field. The maximum field strength of the electromagnet used (3472-10 GMW) from Magnet Systems was 2.1 T. The sample was exposed to a vibration frequency of 75 Hz, and the hysteresis loops were recorded between $-1.5 \cdot 10^8$ A·m$^{-1}$ and $1.5 \cdot 10^8$ A·m$^{-1}$.

TEM Measurements

The TEM measurements were carried out on a Leo 912 Omega from Zeiss. For this purpose, the samples were dripped from a particle dispersion onto a carbon-coated copper grid before the measurements, and the samples were dried at room temperature. The images were evaluated using SiViewer software and ImageJ software.

SEM Measurements

SEM micrographs were generated using a Zeiss Neon 40 ESB CrossBeam FIB-SEM scanning electron microscope. The samples were dripped from a particle dispersion onto a silica plate. The samples were coated with gold before the measurement. The particle size was evaluated after measurement using ImageJ software.

The invention claimed is:

1. A polymerizable dental material comprising
at least one radically polymerizable compound, and
magnetic particles comprising a magnetic core and a first coating of a first shell material,
wherein a second coating of a second shell material is applied to the surface of the first coating facing away from the core, and
wherein the second shell material is different from the first shell material and has a higher refractive index than the first shell material.

2. The polymerizable dental material according to claim 1,
wherein the ratio of the refractive index of the second shell material of the particles to the refractive index of the first shell material of the particles is from 1.1 to 2.6.

3. The polymerizable dental material according to claim 1,
wherein the ratio of the thickness of the second coating of the particles to the thickness of the first coating of the particles is from 0.1 to 2.5.

4. The polymerizable dental material according to claim 1,
wherein the ratio of the thickness of the second coating of the particles to the radius of the first coating of the particles is from 0.1 to 2.5.

5. The polymerizable dental material according to claim 1,
wherein the second shell material of the particles is selected from the group consisting of $TiO_2$, $ZrO_2$, ZnS, $Al_2O_3$, poly(pentabromophenyl methacrylate) and mixtures thereof.

6. The polymerizable dental material according to claim 1,
wherein the first shell material of the particles is selected from the group consisting of $SiO_2$, $SiO_2$ acrylate, polystyrene, polymethyl methacrylate, polyvinyl alcohol, polyalkyl acrylate, polycarbonate, $MgF_2$, fluorinated polymer, $Al_2O_3$, ZnO and mixtures thereof.

7. The polymerizable dental material according to claim 1,
wherein the first shell material of the particles is $SiO_2$ and the second shell material is $TiO_2$.

8. The polymerizable dental material according to claim 1,
wherein the magnetic core of the particles comprise a metal oxide selected from the group consisting of (i) iron oxide, (ii) ferrites of the general formula $MeO \cdot Fe_2O_3$ wherein Me is selected from the group consisting of Ni, Zn, Mn, Co, Cu, Mg, Cd, Ba and Sr, (iii) mixed ferrites of the general formula $Me_yFe_{3-y}O_4$, wherein Me is selected from the group consisting of Ni, Zn, Mn, Co, Cu, Mg, Cd, Ba and Sr and y is between 0 and 1, (iv) oxides of Co, Ni and Nd and (v) $CrO_2$.

9. The polymerizable dental material according to claim 8,
wherein the magnetic core of the particles comprises $CrO_2$.

10. The polymerizable dental material according to claim 1,
in which the particles have an average diameter of from 10 to 2000 nm.

11. The polymerizable dental material according to claim 1, wherein the ratio of the refractive index of the second shell material to the refractive index of the first shell material is from 1.6 to 1.8.

12. The polymerizable dental material according to claim 1, wherein the ratio of the thickness of the second coating of the particles to the thickness of the first coating of the particles is from 1.0 to 2.0.

13. The polymerizable dental material according to claim 1, wherein the ratio of the thickness of the second coating of the particles to the radius of the first coating of the particles is from 1.0 to 2.0.

14. The polymerizable dental material according to claim 1, in which the particles have an average diameter of from 300 to 1000 nm.

* * * * *